United States Patent [19]

Hestermann et al.

[11] 4,122,123

[45] Oct. 24, 1978

[54] PRODUCTION OF QUATERNARY PHOSPHONIUM HALIDES

[75] Inventors: Klaus Hestermann, Erftstadt Bliesheim; Horst Staendeke, Bruhl; Bernd Lippsmeier, Hurth-Knapsack, all of Fed. Rep. of Germany

[73] Assignee: Hoechst Aktiengesellschaft, Frankfurt am Main, Fed. Rep. of Germany

[21] Appl. No.: 635,587

[22] Filed: Nov. 28, 1975

[30] Foreign Application Priority Data

Dec. 5, 1974 [DE] Fed. Rep. of Germany ........ 2457442
Mar. 19, 1975 [DE] Fed. Rep. of Germany ........ 2511933
May 17, 1975 [DE] Fed. Rep. of Germany ........ 2522021

[51] Int. Cl.$^2$ .................................................. C07F 9/54
[52] U.S. Cl. ........................ 260/606.5 F; 260/606.5 P
[58] Field of Search .................... 260/606.5 F, 606.5 P

[56] References Cited

U.S. PATENT DOCUMENTS

| | | | |
|---|---|---|---|
| 3,030,421 | 4/1962 | Reuter et al. ................... | 260/606.5 P |
| 3,316,293 | 4/1967 | Carr et al. ...................... | 260/606.5 F |
| 3,389,183 | 6/1968 | Hays ............................... | 260/606.5 P |
| 3,755,460 | 8/1973 | Staendeke ...................... | 260/606.5 F |
| 3,760,001 | 9/1973 | Staendeke ...................... | 260/606.5 P |
| 4,073,810 | 2/1978 | Hestermann et al. .......... | 260/606.5 P |

OTHER PUBLICATIONS

Kosolopoff et al., Arg. Phas. Cpds., Wiley Intersc., John Wiley & Sons, N. Y., vol. 2, pp. 190–194; vol. 3, pp. 349–354; VI pp. 7, 8, 10, 16, 21, 22, 24, 25, 30, 37 to 40, (1972).

Primary Examiner—Helen M. S. Sneed
Attorney, Agent, or Firm—Connolly and Hutz

[57] ABSTRACT

Production of quaternary phosphonium halides of the general formula:

$$[R^1R^2R^3R^4P]X,$$

in which $R^1$, $R^2$, $R^3$ and $R^4$ stand for identical or different alkyl groups having from 1 to 4 carbon atoms and X stands for halogen, especially for chlorine or bromine. The compounds are more especially made by flowing hydrogen phosphide or a primary phosphine $R^1PH_2$ or secondary phosphine $R^1R^2PH$ or tertiary phosphine $R^1R^2R^3P$ and an alkyl halide $R^4X$ in a molar ratio from 0.02 to 10, at a temperature from 100° to 500° C, under a pressure of up to 10 atmospheres gauge and for a period from 0.5 to 500 seconds over a catalyst and separating the resulting quaternary phosphonium halides from the reaction gas.

The halides so made are used for making trialkylphosphine oxides and trialkylphosphines.

13 Claims, No Drawings

PRODUCTION OF QUATERNARY PHOSPHONIUM HALIDES

The present invention relates to a novel process for making quaternary phosphonium halides of the general formula $$[R^1R^2R^3R^4P]X,$$

in which $R^1$, $R^2$, $R^3$ and $R^4$ stand for identical or different alkyl groups having from 1 to 4 carbon atoms and X stands for a halogen atom, especially for a chlorine or bromine atom, and to the use of the compounds so made.

Quaternary phosphonium halides are commonly made by reacting a tertiary phosphine with a hydrocarbon halide in accordance with the following equation:

$$R_3P + RX = [R_4P]X$$

in which R stands for a hydrocarbon and X stands for halogen.

Tetramethylphosphonium iodide is more especially produced from trimethyl phosphine and methyl iodide in etheral dilution (J. Chem. Soc. (London), 1929, pages 2342, and 1933, page 989).

A further process describes the additive combination of tertiary phosphines with compounds having an activated double bond in the presence of a mineral acid, in accordance with the following equation:

$$R_3P + CH_2 = CH-CN + HBr =$$
$$[R_3P-CH_2-CH_2-CN]Br.$$

(Chem. Berichte 94 (1961), page 1331 and German Published Specification "Auslegeschrift" No. 1 045 401).

These two processes are, however, not fully satisfactory inasmuch as very expensive tertiary phosphines are required to be used as starting materials therein.

It is also known that phosphonium halides can be mode by reacting an alkyl halide with white phosphorus at 260° C in a bomb tube (cf. German Published Specification "Auslegeschrift" No. 1 294 376).

This latter process is carried out under pressure, which is disadvantageous. It is also known that quaternary phosphonium halides can be produced by reacting a phosphine, a primary or secondary phosphine (in which phosphines the hydrogen is fully replaced by a metal) with an alkylene halide (Chem. Berichte 92 (1959), pages 1118 and 2088).

$$Me_3P + 4 RX = [R_4P] X + 3 MeX$$

$$Me_2PR + 3 RX = [R_4P] X + 2 MeX$$

$$MePR_2 + 2 RX = [R_4P] X + MeX$$

(Me = alkali metal; R = alkyl radical; X = halogen)

In this process it is necessary first to prepare the alkali metal phosphides in a very expensive separate operation in liquid ammonia with the use of alkali metals, which are difficult to handle. The direct alkylation of free phosphine or free primary and secondary alkyl phosphines has long been held impossible in the literature (cf. Houben-Weyl, "Methoden der Organischen Chemie", vol. XII/I (1963), page 97).

In clear contrast with this, the present invention now unexpectedly provides a process for making quaternary phosphonium halides of the general formula $[R^1R^2R^3R^4P]X$, in which $R^1$, $R^2$, $R^3$ and $R^4$ stand for identical or different alkyl groups having from 1 to 4 carbon atoms and X stands for halogen, especially chlorine or bromine, by reacting a phosphine $PH_3$, primary phosphine $R^1PH_2$, secondary phosphine $R^1R^2PH$ or tertiary phosphine $R^1R^2R^3P$, in which $R^1$, $R^2$ and $R^3$ stand for identical or different alkyl groups having from 1 to 4 carbon atoms with on alkyl halide $R^4X$, in which $R^4$ stands for an alkyl group having from 1 to 4 carbon atoms and X stands for halogen, especially chlorine or bromine, which process comprises: flowing hydrogen phosphide or a primary phosphine $R^1PH_2$ or secondary phosphine $R^1R^2PH$ or tertiary phosphine $R^1R^2R^3P$ and an alkyl halide $R^4X$ in a molar ratio from 0.02 to 10, preferably 0.05 to 2, at temperatures from 100° to 500° C, preferably 150° to 350° C, under a pressure of up to 10 atmospheres gauge, preferably at atmospheric pressure, for a period from 0.5 to 500 seconds, preferably 10 to 200 seconds, over a catalyst and separating the resulting quaternary phosphonium halides from the reaction gas.

The above reaction may be effected in a fixed bed reactor as well as in a flow bed reactor.

Active carbon, especially active carbon having a BET-surface area of more than 10 m²/g, is particularly well adapted for use as a catalyst. It is good practice to employ the active carbon in the form of particles having a size from 0.1 to 10 mm, for use in a fixed bed reactor, and to employ pulverulent active carbon, for use in a flow bed reactor. Further useful catalysts comprise metals belonging to the first or eighth subgroup of the Periodic System of the elements, which may be used alone or in combination, e.g. gold, platinum or palladium. It is possible for these metals to be deposited on a carrier being inert under the reaction conditions, such as $Al_2O_3$ or $SiO_2$, for example.

Needless to say unreacted starting material issuing from the reactor may be separated from the quaternary phosphonium halides and then recycled to be used again in the process.

The reactions which occur in the reactor are believed to be based on the following empirical formulae:

$$PH_3 + 4 R^4X = [R_4^4P] X + 3 HX$$

$$R^1PH_2 + 3 R^4X = [R^1R_3^4P] X + 2 HX$$

$$R^1R^2PH + 2 R^4X = [R^1R^2R_2^4P] X + HX$$

$$R^1R^2R^3P + R^4X = [R^1R^2R^3R^4P] X$$

As results it is possible, depending on the phosphine used as starting material in each particular case, to produce symmetric quaternary phosphonium halides having identical or different alkyl groups linked thereto. In carrying out the present process, it is immaterial whether the starting material is used in admixture with one or more inert gases. Those quaternary phosphonium halides, which have a melting point lower than the reaction temperature, are separated from the reaction gas downstream of the catalyst by condensation and purified in known manner, e.g. by extraction and recrystallization. In those cases in which melting point and vapor pressure of the quaternary phosphonium halides do not permit removing them from the reactor during the reaction at the temperature selected, the catalyst is allowed to become saturated with the particular phosphonium halide, whereupon the reaction is interrupted. Following this, the catalyst is treated in known fashion, e.g. with the aid of water or alcohol or another suitable solvent, so as to dissolve the phosphonium halide thereon, which is then separated from the resulting solution, if desired after evaporation of the solvent. Once the solvent has been expelled, it is possible for the catalyst so reactivated, which need not be removed from the reactor, to be used again.

The process of the present invention, which is naturally not limited to the embodiment specifically described herein, enables quaternary phosphonium halides to be produced in commercial quantities from readily accessible alkyl halides $R^4X$ and hydrogen phosphide, which is a by-product being obtained in commercial quantities in the production of sodium hypophosphite, and from the following organophosphines: $R^1PH_2$; $R^1R^2PH$ and $R^1R^2R^3P$, which in turn are readily obtainable by the process described in Belgian Pat. No. 825 541. The quaternary phosphonium halides produced in accordance with the present invention are important intermediates in the field of flame-proofing agents and extractants, for example.

A further object of the present invention relates to the use of tetralkylphosphonium halides made in accordance therewith for the production of trialkyl phosphine oxides of the general formula $R^1R^2R^3PO$, in which $R^1$, $R^2$ and $R^3$ have the meanings given hereinabove.

It has been described that trialkylphosphine oxides, for example, can be made by oxidizing trialkylphosphines or by subjecting tetralkylphosphonium hydroxides to thermal decomposition. Further known processes describe the reaction of phosphorus halides with organo-metal compounds, e.g. $P(O)X_3 + 3\ RMgX \rightarrow R_3P(O) + 3MaX_2$, or the additive combination of olefins, aldehydes or ketones with primary or secondary phosphine oxides, e.g. $R_2{}^1P(O)H + R_2CH = CH_2 \rightarrow R_2{}^1P(O)R^3$. (G. M. Kosolapoff and L. Maier, Organic Phosphorus Compounds, Vol. 3, Wiley-Interscience, New York (1972)).

These however are processes which can scarcely be effected on a commercial scale inasmuch as they use starting material, which is prepared in a plurality of processing stages and therefore very expensive.

We have now unexpectedly found that trialkylphosphine oxides are readily obtainable from hydrogen phosphide, primary, secondary or tertiary phosphines provided that the tetralkylphosphonium halides made in accordance with the present invention are used as the starting an for making the said phosphine oxides. To this end, the tetralkylphosphonium halides are first reacted in known manner with an alkali metal hydroxide, then neutralized and trialkylphosphine oxide is separated from the neutralized material.

It is technically good practice to effect the alkaline hydrolysis at elevated temperature so as to arrive at the tertiary phosphine oxide stage via the tetralkylphosphonium halide stage.

The hydrolysis is believed to initially cause the formation of tetralkylphosphonium hydroxides which are transformed later into trialkylphosphine oxides, while an alkane is eliminated. The following empirical formulae are a diagrammatic representation of the reaction which occurs:

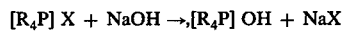

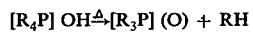

(G. M. Kosolapoff and L. Maier, Organic Phosphorus Compounds, vol. 2, Wiley-Interscience, New York (1972)).

Pure trialkylphosphine oxide is obtained by suspending tetralkylphosphonium chloride, which may have been separated earlier, in a 40–50% sodium hydroxide solution and reacting the suspension at 120°–150° C. The resulting phosphine oxide solution is neutralized by means of hydrochloric acid and then evaporated to dryness. The evaporation residue is taken up in anhydrous ethanol and freed from sodium chloride by filtration. Once the solvent has been distilled off, pure trialkylphosphine oxide is obtained.

The process of the present invention is the first to permit the production of low tertiary phosphine oxides from hydrogen phosphide via the tetralkylphosphonium chloride stage, which is a very desirable step forward in the art.

Trialkylphosphine oxides find widespread uses as detergents, dyeing auxiliaries, catalysts, corrosion inhibitors and as interesting intermediates for the production of flameproofing agents, plant protective agents and pharmaceutical preparations.

The present invention also relates to the use of the tetralkylphosphonium halides of the present invention for making trialkylphosphines of the general formula $R^1R^2R^3P$, in which $R^1$, $R^2$ and $R^3$ have the meanings given hereinabove.

It has been described that trialkylphosphines can be made by reacting a phosphorus halide with an organometal compound, e.g. in accordance with the following equation:

$$PX_3 + 3\ RMgX \rightarrow R_3P + 3\ MgX_2$$

Further known processes are based on the alkylation of phosphines, the additive combination of olefins, aldehydes or ketones with phosphines, e.g. in accordance with the following equation:

$$R^1PH + 2'R^2CH{=}CH_2 \rightarrow R^1PR_2{}^{'3},$$

or the reduction of phosphine oxides and phosphine sulfides (G. M. Kosolapoff and L. Maier, Organic Phosphorus Compounds, vol. 1, Wiley-Interscience, New York (1972)).

These are processes which can scarcely be effected on a commercial scale inasmuch as they use starting material which is prepared by a plurality of steps and therefore very expensive.

We have now unexpectedly found that trialkylphosphines are readily obtainable from hydrogen phosphide, primary, secondary or tertiary phosphines provided that the tetralkylphosphonium halides of the present invention are used as the starting material for making the said phosphines.

To this end, the tetralkylphosphonium halides are heated in contact with a stream of an inert gas to temperatures higher than 300° C, the resulting trialkylphosphonium halides and/or trialklphosphines are absorbed, preferably in hydrochloric acid, and the resulting trialkyl phosphonium halide solution is treated in known manner, e.g. by adding an alkali metal hydroxide thereto, so as to liberate and separate the trialkylphosphines therefrom.

The starting material should preferably be heated to temperatures from 380° to 480° C, more preferably 400° to 420° C, and with the use of nitrogen as the inert gas.

The trialkylphosphines are easy to liberate from the trialkylphosphonium halide solution in hydrochloric acid by admixing the solution with an alkali metal hydroxide solution so as to establish a pH from 12 to 14.

The trialkylphosphines set free in the manner just described are separated from the alkaline solution in accordance with their respective boiling points, i.e. by distillation where low-boiling products are concerned, or by extraction where high-boiling products are concerned.

The trialkylphosphine and/or trialkylphosphonium halide are often obtained together with an alkyl halide-/alkane/hydrogen halide-mixture. The following empirical formulae are a diagrammatic representation of the reactions which occur:

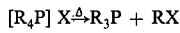

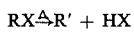

(G. M. Kosolapoff and L. Maier, Organic Phosphorus Compounds, vol. 1, Wiley-Interscience, New York (1972)).

By such use of the tetralkylphosphonium halides made in accordance with the present invention it is for the first time possible to produce low tertiary phosphines from hydrogen phosphide. Trialkylphosphines find widespread uses as catalysts, e.g. in the form of complex compounds with transition metal compounds in the cyclization of ethylene and acetylene compounds, in the polymerization of aldehydes, ethylene and acetylene compounds, in the hydroformylation, and in the dehalogenation of halohydrocarbons.

EXAMPLE 1

Tetramethylphosphonium chloride [$(CH_3)_4P$]Cl was prepared. To this end, 20 l/hr of $PH_3$ and 100 l/hr of $CH_3Cl$ were mixed together and preheated to 200° C. The resulting mixture was passed at 280° C and at atmospheric pressure through a reactor filled with active carbon and contacted therewith for a period of 210 seconds. The supply of the $PH_3/CH_3Cl$-mixture was terminated after 85 hours. This corresponded to the absorbing power of the quantity of active carbon placed in the reactor. Nitrogen was also passed through the reactor for a period of 2 hours at 280° C. Following this, tetramethylphosphonium chloride having a melting point higher than 400° C was removed from the active carbon by treating it with warm water having a temperature of 90° C. The resulting aqueous solution was evaporated to dryness, the tetramethylphosphonium chloride was taken up in ethanol, precipitated with diethylether and thereby purified. 2 605 g of $PH_3$ gave 8 052 g of [$(CH_3)_4P$]Cl. This corresponded to a yield of 83%. 285 g of yellow phosphorus and a mixture of $CH_3PH_2$, $(CH_3)_2PH$ and $(CH_3)_3P$ were obtained as by-products. These latter compounds can be used once again as starting materials for making [$(CH_3)_4P$]Cl, or separated and worked up by the process described in Belgian Patent 825 541 and made into valuable material for use in the production of flame-proofing agents, for example.

EXAMPLE 2

Tetramethylphosphonium chloride [$(CH_3)_4P$]Cl was made. To this end 25 l/hr of $CH_3PH_2$ and 100 l/hr of $CH_3Cl$ were mixed together and preheated to 150° C. The mixture so made was passed at 280° C and at atmospheric pressure through a reactor filled with active carbon and contacted therewith for a period of 120 seconds. The supply of the $CH_3PH_2/CH_3Cl$-mixture was terminated after 35 hours. The other conditions were the same as those described in Example 1. 1 785 g of $CH_3PH_2$ gave 2 705 g of [$(CH_3)_4P$]Cl, corresponding to a yield of 78%.

EXAMPLE 3

Tetramethylphosphonium chloride [$(CH_3)_4P$]Cl was made. To this end 25 l/hr of $(CH_3)_2PH$ and 75 l/hr of $CH_3Cl$ were mixed together and preheated to 150° C. The resulting mixture was passed at 280° C and at atmospheric pressure through a reactor filled with active carbon and contacted therewith for a period of 50 seconds. The supply of the $(CH_3)_2PH/CH_3Cl$-mixture was terminated after 17 hours. The other conditions were the same as those described in Example 1. 1 189 g of $(CH_3)_2PH$ gave 2 062 g of [$(CH_3)_4P$]Cl, corresponding to a yield of 85%.

EXAMPLE 4

Tetramethylphosphonium chloride [$(CH_3)_4P$]Cl was made. To this end, 25 l/hr of $(CH_3)_3P$ and 50 l/hr of $CH_3Cl$ were mixed together and preheated to 150° C. The resulting mixture was passed at 270° C and at atmospheric pressure through a reactor filled with active carbon and contacted therewith for a period of 18 seconds. The supply of the $(CH_3)_3P/CH_3Cl$-mixture was terminated after 8.5 hours. The other conditions were the same as those described in Example 1. 645 g of $(CH_3)_3P$ gave 977 g of [$(CH_3)_4P$]Cl, corresponding to yield of 91%.

EXAMPLE 5

Preparation of trimethylphosphine oxide

Tetramethylphosphonium chloride [$(CH_3)_4P$]Cl was first prepared. To this end 20 l/hr of $PH_3$ and 100 l/hr of $CH_3Cl$ were mixed together and preheated to 200° C. The resulting mixture was passed at 280° C and at atmospheric pressure through a reactor filled with active carbon and contacted therewith for a period of 210 seconds. The supply of the $PH_3/CH_3Cl$-mixture was terminated after 85 hours. This corresponded to the absorbing power of the quantity of active carbon placed in the reactor. Nitrogen was also passed through the reactor for a period of 2 hours at 280° C. Following this, tetramethylphosphonium chloride having a melting point higher than 400° C was removed from the active carbon by treating it with warm water having a temperature of 90° C. The resulting aqueous solution was evaporated to dryness, the tetramethylphosphonium chloride was taken up in ethanol, precipitated with diethylether and thereby purified. 2 605 g of $PH_3$ gave 8 052 g of [$(CH_3)_4P$]Cl, corresponding to a yield of 83%.

The product so obtained was analyzed and found to contain:

Phosphorus: 24.5 weight % of P (calculated 24.47 weight %)

Chlorine: 28.1 weight % of Cl (calculated 28.01 weight %)

Alkaline hydrolysis: 8.504 g of [$(CH_3)_4P$]Cl was treated with 25 cc of a 50 weight % NaOH-solution at 120° C. 1610 cc of gas (at 20° C under 768 mm Hg) was collected. Gas chromatography indicated that the gas contained more than 99.9% by volume of methane. The purity of the product accordingly was 100.00%.

The product was used for making trimethylphosphine oxide. To this end, 30 g of [(CH₃)₄P]Cl was suspended in 80 g of a 50 weight % sodium hydroxide solution (molar ratio of NaOH to phosphonium salt = 4:1) and reacted at 120°–130° C. Once gas ceased to be evolved, the whole was neutralized with the use of hydrochloric acid and a pH-electrode, and the solution was evaporated in a rotating evaporator. The residue was taken up in anhydrous ethanol, sodium chloride was filtered off and the solvent was distilled off. (CH₃)₃P(O) was obtained in a yield of 18 g, corresponding to a yield of 83% of the theoretical.

The following further experiments, in which [(CH₃)₄P]Cl and NaOH were used in various molar ratios, were made under the conditions just described.

| Exp. No. | (CH₃)₄P Cl mol | NaOH mol | Reaction temp. °C | Yield of (CH₃)P(O) |
|---|---|---|---|---|
| 2 | 1.00 | 4 | 125 | 84% |
| 3 | 0.40 | 1 | 130 | 94% |
| 4 | 0.40 | 0.8 | 120 | 100% |

EXAMPLE 6

Preparation of trimethylphosphine oxide

Tetramethylphosphonium chloride was prepared first [(CH₃)₄P]Cl. To this end, 20 l/hr of PH₃ and 100 l/hr of CH₃Cl were mixed together and preheated to 200° C. The resulting mixture was passed at 280° C and at atmospheric pressure through a reactor filled with active carbon and contacted therewith for a period of 210 seconds. The supply of the PH₃/CH₃Cl-mixture was terminated after 85 hours. This corresponded to the absorbing power of the quantity of active carbon placed in the reactor. Nitrogen was also passed through the reactor for 2 hours at 280° C. Following this, the tetramethylphosphonium chloride having a melting point higher than 400° C was eluted from the active carbon by means of warm water having a temperature of 90° C.

While the tetramethylphosphonium chloride was left unseparated, the aqueous [(CH₃)₄P]Cl solution was treated with a 40 weight % sodium hydroxide solution and a pH-value of 12 was established with the aid of a pH-electrode. By heating the solution for about 1 hour to 80° C while gaseous nitrogen was passed therethrough, it was freed from minor proportions of monomethylphosphine, dimethylphosphine and trimethylphosphine. NMR-spectroscopy showed that this was sufficient to effect the conversion of a proportion as high as 4 weight % based on the [(CH₃)₄P]Cl used, into trimethylphosphine oxide. The solution was then concentrated in a rotating evaporator until NaCl commenced separation and thereafter reacted with 2 mols of sodium hydroxide per mol of [(CH₃)₄P]Cl. Once gas ceased to be evolved, the solution was neutralized by means of hydrochloric acid, evaporated to dryness and taken up in anhydrous ethanol. The sodium chloride was filtered off and the solvent was distilled off. 5 520 g of trimethylphosphine oxide was obtained. This corresponded to a yield of 77%, based on the phosphine used.

EXAMPLE 7

Preparation of trimethylphosphine

Trimethylphosphonium chloride [(CH₃)₄P]Cl was prepared first. To this end, 20 l/hr of PH₃ and 100 l/hr of CH₃Cl were mixed together and preheated to 200° C. The resulting mixture was passed at 280° C and at atmospheric pressure through a reactor filled with active carbon, and contacted therewith for a period of 210 seconds. The supply of the PH₃/CH₃Cl mixture was terminated after 85 hours. This corresponded to the absorbing power of the quantity of active carbon placed in the reactor. Nitrogen was also passed through the reactor at 280° C over a period of 2 hours. Following this, tetramethylphosphonium chloride melting at a temperature higher than 400° C was removed from the active carbon by washing with warm water having a temperature of 90° C. The resulting aqueous solution was evaporated to dryness, the tetramethylphosphonium chloride was taken up in ethanol, precipitated with diethylether and purified in this manner. 2 605 g of PH₃ gave 8 052 g of (CH₃)₄P Cl, corresponding to a yield of 83%.

The product so made was analyzed and found to contain 24.5 weight % of P (calculated: 24.47 weight %) and 28.1 weight % of Cl (calculated: 28.01 weight %).

Alkaline hydrolysis: 8.504 g of [(CH₃)₄P]Cl was treated with 25 cc of a 50 weight % NaOH-solution at 120° C. 1610 cc of gas (at 20° C under 768 mm Hg) was collected. Gas chromatography indicated that the gas contained more than 99.9% by volume of methane. The product was substantially 100% pure.

The product was used for making trimethylphosphine. To this end, 24.3 g of [(CH₃)₄P]Cl was pyrolyzed in a tubular reactor heated to 420° C and in contact with a stream of nitrogen (20 l/hr The resulting phosphorus-containing reaction products were absorbed in gas-washing bottles (filled with concentrated hydrochloric acid) downstream of the reactor. The solutions absorbed therein were delivered to a distilling apparatus, treated therein with a 40 weight % sodium hydroxide solution so as to establish a pH-value of 12–14 and heated to 100° C. Trimethylphosphine which distilled off ($bp_{760}$ = 40° C) was condensed at −30° C and absorbed in toluene. Gas chromatography indicated that the material contained 11.4 g of trimethylphosphine, corresponding to a yield of 78% of the theoretical.

We claim:

1. In the process for making quaternary phosphonium halides of the general formula:

[R₄P] X in which R is identical or different alkyls having from 1 to 4 carbons and X is chlorine or bromine, the improvement which comprises reacting hydrogen phosphide as starting material with an alkyl halide RX, R and X having the meaning given above in a molar ratio from 0.02 to 10, at a temperature from 100° to 500° C, within a gas atmosphere inert to the reaction mixture, under a pressure of up to 10 atmospheres gauge and for a period of time of about 210 seconds by flowing the gaseous reactants over a catalyst selected from the group consisting of active carbon, a finely divided metal from the first or eighth subgroup of the Periodic System of the elements and mixture of such metals; and separating the resulting quaternary phosphonium halides from the reaction gas.

2. The process as claimed in claim 1, wherein the hydrogen phosphide and the alkyl halide are used in a molar ratio from 0.05 to 2.

3. The process as claimed in claim 1, wherein the starting materials are passed over the catalyst at temperatures from 150° to 350° C.

4. The process as claimed in claim 1, wherein the starting materials are passed over the catalyst at atmospheric pressure.

5. The process as claimed in claim 1, wherein the active carbon catalyst has a BET-surface area of more than 10 m$^2$/g.

6. The process as claimed in claim 1, wherein the reaction is effected in a fixed bed reactor with the use of particulate active carbon having a particle size from 0.1 to 10 mm.

7. The process as claimed in claim 1, wherein the reaction is effected in a flow bed reactor with the use of pulverulent active carbon.

8. The process as claimed in claim 1, wherein gold, palladium or platinum is used as the said metal catalyst.

9. The process as claimed in claim 1, wherein the said metal catalyst is deposited on a carrier.

10. The process as claimed in claim 9, wherein the carrier is $Al_2O_3$, $SiO_2$ or a mixture thereof.

11. The process as claimed in claim 1, wherein quaternary phosphonium halides having a melting point lower than the reaction temperature are removed from the reaction gases downstream of the catalyst by condensation.

12. The process as claimed in claim 1, wherein quaternary phosphonium halides of which melting point and vapor pressure forbid removing them from the reactor during the reaction, are separated from the reaction gases by allowing the catalyst to become saturated with the resulting particular phosphonium halide, interrupting the reaction, removing the reaction product on the catalyst by treatment with a suitable solvent and separating the phosphonium halides from the resulting solution by removing the solvent.

13. The process as claimed in claim 1, wherein the starting materials are mixed together and preheated to about 150° C and the resulting mixture is passed over the catalyst.

* * * * *